United States Patent
Oguri et al.

(10) Patent No.: US 10,293,628 B2
(45) Date of Patent: May 21, 2019

(54) RECORDING MEDIUM AND SILANE COUPLING AGENT

(71) Applicant: CANON KABUSHIKI KAISHA, Tokyo (JP)

(72) Inventors: Isamu Oguri, Fukushima (JP); Hisao Kamo, Ushiku (JP); Tetsuro Noguchi, Hachioji (JP); Masahito Miyabe, Yokohama (JP); Naoya Hatta, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/548,073

(22) PCT Filed: Jan. 27, 2016

(86) PCT No.: PCT/JP2016/000400
§ 371 (c)(1),
(2) Date: Aug. 1, 2017

(87) PCT Pub. No.: WO2016/125459
PCT Pub. Date: Aug. 11, 2016

(65) Prior Publication Data
US 2018/0022139 A1   Jan. 25, 2018

(30) Foreign Application Priority Data
Feb. 4, 2015 (JP) .................. 2015-020526

(51) Int. Cl.
  *B41M 5/00* (2006.01)
  *B41M 5/52* (2006.01)
  *D21H 19/38* (2006.01)
  *C07F 7/08* (2006.01)
  *D21H 17/67* (2006.01)
  *D21H 17/68* (2006.01)
  *D21H 19/12* (2006.01)

(52) U.S. Cl.
CPC ............ *B41M 5/5227* (2013.01); *B41M 5/52* (2013.01); *C07F 7/0836* (2013.01); *D21H 17/67* (2013.01); *D21H 17/68* (2013.01); *D21H 19/12* (2013.01); *D21H 19/38* (2013.01); *B41M 5/529* (2013.01); *B41M 5/5218* (2013.01)

(58) Field of Classification Search
CPC .. B41M 5/5218; B41M 5/5227; C07F 7/0836; D21H 19/12
See application file for complete search history.

(56) References Cited

U.S. PATENT DOCUMENTS

| | | | |
|---|---|---|---|
| 8,979,996 B2 | 3/2015 | Standke | |
| 2004/0121094 A1* | 6/2004 | Aert | B41M 5/52 428/32.1 |
| 2006/0013971 A1* | 1/2006 | Chen | B41M 5/52 428/32.34 |
| 2013/0167754 A1 | 7/2013 | Wassmer et al. | |

FOREIGN PATENT DOCUMENTS

| | | |
|---|---|---|
| EP | 1403091 A2 | 3/2004 |
| JP | H07-232473 A | 9/1995 |
| JP | S61-10483 A | 1/1996 |
| JP | H08-132731 A | 5/1996 |
| JP | H09-066664 A | 3/1997 |
| JP | H09-76628 A | 3/1997 |
| JP | 2000-211235 A | 8/2000 |
| JP | 2002-211111 A | 7/2002 |
| JP | 2004-067925 A | 3/2004 |
| JP | 2004-124000 A | 4/2004 |
| JP | 2012-524163 A | 10/2012 |
| JP | 2013-535431 A | 9/2013 |

OTHER PUBLICATIONS

Bijay P. Tripathi, et al., Organic-inorganic hybrid alkaline membranes by epoxide ring opening for direct methanol fuel cell applications; Journal of Membrane Science, vol. 360, pp. 90-101 (2010).

Sergey Shishatskiy, et al., Quaternary ammonium membrane materials for $CO_2$ separation; Journal of Membrane Science, vol. 359, pp. 44-53 (2010).

* cited by examiner

*Primary Examiner* — Betelhem Shewareged
(74) *Attorney, Agent, or Firm* — Canon U.S.A. Inc., IP Division

(57) ABSTRACT

To provide a recording medium in which the ink absorbability and the color development properties of an image to be obtained are high and in which cracking in an ink receiving layer is sufficiently suppressed.

A recording medium contains a base material and an ink receiving layer containing inorganic particles and a binder, in which the inorganic particles have an organosilicon structure having a quaternary ammonium group, an imino group or a substituted imino group, and a hydroxyl group.

5 Claims, No Drawings

RECORDING MEDIUM AND SILANE COUPLING AGENT

CROSS-REFERENCE TO RELATED APPLICATIONS

This application is a National Stage filing of International Application No. PCT/JP2016/000400 filed Jan. 27, 2016, which claims the benefit of Japanese Patent Application No. 2015-020526, filed Feb. 4, 2015, the disclosures of each of which are hereby incorporated by reference herein in their entirety.

TECHNICAL FIELD

The present invention relates to a recording medium and a silane coupling agent.

BACKGROUND ART

A recording medium having an ink receiving layer containing inorganic particles has been used because the ink absorbability and the color development properties of an image to be obtained are high. Such a recording medium is obtained by applying a coating liquid for ink receiving layer, in which inorganic particles are dispersed, to a base material. However, unless the dispersion stability of the inorganic particles in the coating liquid for ink receiving layer is sufficient, cracking has occurred in the surface in the formation of the ink receiving layer or, the ink absorbability and the color development properties of an image to be obtained have been lowered due to non-uniform dispersion of the inorganic particles in the ink receiving layer in some cases.

Then, an examination on a dispersant capable of stably dispersing inorganic particles in a coating liquid has been performed (Japanese Patent Laid-Open No. 2000-211235, PCT Japanese Translation Patent Publication No. 2012-524163, and PCT Japanese Translation Patent Publication No. 2013-535431). As the dispersant, Japanese Patent Laid-Open No. 2000-211235 describes a cationic polymer having a constituent unit of a polydiallylamine derivative, PCT Japanese Translation Patent Publication No. 2012-524163 describes a composition containing a quaternary amino functional organosilicon compound, and PCT Japanese Translation Patent Publication No. 2013-535431 describes a composition containing a quaternary amino alcohol functional organosilicon compound.

CITATION LIST

Patent Literature

PTL 1: Japanese Patent Laid-Open No. 2000-211235
PTL 2: PCT Japanese Translation Patent Publication No. 2012-524163
PTL 3: PCT Japanese Translation Patent Publication No. 2013-535431

SUMMARY OF INVENTION

The recording medium according to the present invention has a base material and an ink receiving layer containing inorganic particles and a binder, in which the inorganic particles have an organosilicon structure having a quaternary ammonium group, an imino group or a substituted imino group, and a hydroxyl group.

The silane coupling agent according to the present invention, is used for a recording medium having a base material and an ink receiving layer containing inorganic particles and a binder and which has a structure represented by General Formula (1)' shown below,

[Chem.1]

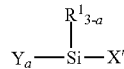

General Formula (1)

wherein, in General Formula (1)', $R^1$ is an alkyl group or an aryl group having 1 to 8 carbon atoms, X represents a structure represented by General Formula X shown below, Y represents a hydrolyzable group, and a is 1, 2, or 3,

[Chem.2]

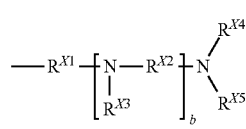

General Formula X wherein, in General Formula X, $R^{X1}$ and $R^{X2}$ each independently represent an alkylene group or an arylene group having 2 to 8 carbon atoms, at least one selected from $R^{X3}$, $R^{X4}$, and $R^{X5}$ represents a structure represented by General Formula Q shown below and other elements represent a hydrogen atom or an alkyl group or an aryl group having 1 to 8 carbon atoms, and b is an integer of 0 to 5,

[Chem.3]

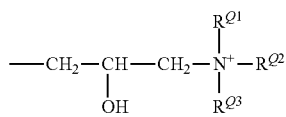

General Formula Q wherein, in General Formula Q, $R^{Q1}$, $R^{Q2}$, and $R^{Q3}$ each independently represent an alkyl group or an aryl group having 1 to 10 carbon atoms.

The present invention can provide a recording medium in which the ink absorbability and the color development properties of an image to be obtained are high and in which cracking in an ink receiving layer is sufficiently suppressed.

The present invention can provide a silane coupling agent used for the recording medium.

Further features of the present invention will become apparent from the following description of exemplary embodiment.

DESCRIPTION OF EMBODIMENT

According to an examination of the present inventors, with the dispersants described in Japanese Patent Laid-Open No. 2000-211235, PCT Japanese Translation Patent Publication No. 2012-524163, and PCT Japanese Translation Patent Publication No. 2013-535431, the dispersion stability of inorganic particles has improved but has not been sufficient and the ink absorbability of the produced recording medium and the color development properties of an image to be obtained have not reached a level demanded in the present invention and cracking has occurred in an ink receiving layer in some cases.

Therefore, the present invention provides a recording medium in which the dispersion stability of inorganic particles in a coating liquid for ink receiving layer is improved and the ink absorbability and the color development properties of an image to be obtained are high and cracking in an ink receiving layer is sufficiently suppressed. And the present invention provides a silane coupling agent used for the recording medium.

Hereinafter, the present invention is described in detail with reference to a suitable embodiment.

According to an examination of the present inventors, the present inventors have found that, in order to push up the level of each of the ink absorbability of a recording medium and the color development properties of an image to be obtained to a higher level and to sufficiently suppress cracking in an ink receiving layer, it is necessary to consider not only improving the dispersion stability of inorganic particles in a coating liquid for ink receiving layer but the interaction with a coloring material in ink and the interaction with a binder as a binding agent of inorganic particles contained in an ink receiving layer. Then, it has been found that the above-described effects are obtained by blending a material having a specific structure as a coupling agent of inorganic particles and a binder in the ink receiving layer. Specifically, it has been found that it is important to treat the inorganic particles with a silane coupling agent having a quaternary ammonium group, an imino group or a substituted imino group, and a hydroxyl group, i.e., use of inorganic particles having an organosilicon structure having a quaternary ammonium group, an imino group or a substituted imino group, and a hydroxyl group. The presumed mechanism in which the effects of the present invention are obtained by the above-described configuration is as follows. First, the organosilicon structure is introduced by a reaction between hydrolyzable groups of the silane coupling agent and hydroxyl groups of the surface of the inorganic particles. At this time, the dispersion stability of the inorganic particles increases due to the fact that the organosilicon structure introduced into the surface of the inorganic particles has the hydroxyl group. Moreover, due to the fact that the organosilicon structure has the quaternary ammonium group, the interaction with the coloring material in ink increases and the color development properties of an image to be obtained increases. Furthermore, due to the fact that the organosilicon structure has the imino group or the substituted imino group, the stability in a high pH region of a dispersion liquid of the inorganic particles increases. It is presumed that, due to the increase in the dispersion stability of the inorganic particles as described above, cracking in an ink receiving layer is suppressed and further the interaction between the binder and the inorganic particles is strengthened and the ink absorbability and the color development properties of an image to be obtained increase.

Recording Medium

The recording medium of the present invention has a base material and at least one ink receiving layer. In the present invention, the recording medium is suitably an ink jet recording medium for use in an ink jet recording method. Hereinafter, each component configuring the recording medium of the present invention is described.

In the present invention, the arithmetic average roughness Ra (Measurement length: 2.5 mm, Cutoff value: 0.8 mm) defined by JIS B 0601:2001 of the surface of the recording medium is suitably 0.8 µm or more and 2.5 µm or less. By the configuration, the visibility of damages of the surface of the recording medium is effectively suppressed. Examples of a method for adjusting the Ra of the surface of the recording medium include, for example, a method employing a resin-covered base material including pressing the surface of the resin-covered base material with a roll having specific unevenness, and then applying a coating liquid for ink receiving layer onto the resin-covered base material, a method including pressing the surface of a recording medium with a roll having specific unevenness, and the like.

<Base Material>

Examples of the base material include those containing only a base paper and those having a base paper and a resin layer, i.e., one in which a base paper is covered with resin. In the present invention, it is suitable to use the base material having a base paper and a resin layer. In that case, the resin layer may be provided only on one surface of the base paper but is suitably provided on both surfaces.

In the present invention, the arithmetic average roughness Ra (Measurement length: 2.5 mm, Cutoff value: 0.8 mm) defined by JIS B 0601:2001 of the surface of the base material is preferably 1 µm or more and less than 5 µm and more preferably 1 µm or more and 4 µm or less. By the configuration, gloss unevenness between an image recorded region and a non-recorded region can be suppressed. Examples of a method for controlling the arithmetic average roughness Ra of the surface of the base material include a method employing a resin-covered base material including pressing the surface of the resin-covered base material with a roll having specific unevenness and the like.

(Base Paper)

The base paper is made using wood pulp as the main material and, as necessary, adding synthetic pulp, such as polypropylene, and synthetic fibers, such as nylon and polyester. Examples of the wood pulp include leaf bleached kraft pulp (LBKP), leaf bleached sulphite pulp (LBSP), northern bleached kraft pulp (NBKP), northern bleached sulphite pulp (NBSP), leaf dissolving pulp (LDP), northern dissolving pulp (NDP), leaf unbleached kraft pulp (LUKP), northern unbleached kraft pulp (NUKP), and the like. One or two or more kinds thereof can be used as necessary. Among the wood pulp, LBKP, NBSP, LBSP, NDP, and LDP containing short fiber components in a high proportion are suitably used. As the pulp, chemical pulp with few impurities (sulfate pulp and sulfite pulp) is suitable. Moreover, pulp whose degree of whiteness is improved by performing bleaching treatment is also suitable. Into the base paper, a sizing agent, a white pigment, a paper strengthening agent, a fluorescent brightening agent, a moisture maintenance agent, a dispersing agent, a softening agent, and the like may be added as appropriate.

In the present invention, the film thickness of the base paper is preferably 50 µm or more and 250 µm or less and more preferably 90 µm or more and 210 µm or less. In the present invention, the film thickness of the base paper is calculated by the following method. First, the cross section of the recording medium is cut out using a microtome, and then the cross section is observed under a scanning electron microscope. Then, the film thickness of arbitrary 100 or more points of the base paper is measured, and the average value is defined as the film thickness of the base paper. The film thickness of the other layers in the present invention is also calculated by the similar method.

In the present invention, the paper density specified by JIS P 8118 of the base paper is preferably 0.6 g/cm$^3$ or more and 1.2 g/cm³ or less. Furthermore, the paper density is more preferably 0.7 g/cm³ or more and 1.2 g/cm³ or less.

(Resin Layer)

In the present invention, when the base paper is covered with resin, the resin layer may be provided in such a manner as to partially cover the base paper surface. The coverage (Area of base paper surface covered with resin layer/Entire area of base paper surface) of the resin layer is preferably 70% or more, more preferably 90% or more, and particularly preferably 100%, i.e., the entire surface of the base paper surface is covered with the resin layer.

In the present invention, the film thickness of the resin layer is preferably 15 µm or more and 60 µm or less, and more preferably 20 µm or more and 60 µm or less, and particularly preferably 30 µm or more and 45 µm or less. When providing the resin layer on both surfaces of the base paper, it is suitable for the film thickness of each of the resin layers on both surfaces to satisfy the ranges mentioned above.

As the resin for use in the resin layer, a thermoplastic resin is suitable. Examples of the thermoplastic resin include acrylic resin, acrylic silicone resin, polyolefin resin, a styrene-butadiene copolymer, and the like. Among the above, the polyolefin resin is suitably used. In the present invention, the polyolefin resin refers to a polymer containing olefin as a monomer. Specifically, homopolymers and copolymers of ethylene, propylene, isobutylene, and the like are mentioned. As the polyolefin resin, one or two or more kinds thereof can be used as necessary. Among the above, polyethylene is suitably used. As the polyethylene, a low density polyethylene (LDPE) and a high-density polyethylene (HDPE) are suitably used.

In the present invention, the resin layer may contain a white pigment, a fluorescent brightening agent, ultramarine, and the like in order to adjust the opacity, the degree of whiteness, and the hue. Among the above, since the opacity can be improved, the white pigment is suitably used. Examples of the white pigment include a rutile type titanium oxide or an anatase type titanium oxide. In the present invention, the content of the white pigment in the resin layer is suitably 3 g/m² or more and 30 g/m² or less. When providing the resin layer on both surfaces of the base paper, it is suitable that the total content of the white pigments in the two resin layers satisfies the range mentioned above. The content of the white pigment in the resin layer is suitably 25% by mass or less based on the resin content. When the white pigment content is larger than 25% by mass, the dispersion stability of the white pigment is not sufficiently obtained in some cases.

(Ink Receiving Layer)

In the present invention, the ink receiving layer may be a monolayer or a multilayer having two or more layers. The ink receiving layer may be provided only on one surface of the base material or may be provided on both surfaces thereof. In the present invention, the ink receiving layer is suitably provided on both surfaces. The film thickness of the ink receiving layer on one surface of the base material is preferably 15 µm or more and 60 µm or less, and more preferably 30 µm or more and 45 µm or less.

Hereinafter, materials which can be contained in the ink receiving layer are individually described.

(Inorganic Particles Having Organosilicon Structure Having Quaternary Ammonium Group, Imino Group or Substituted Imino Group, and Hydroxyl Group)

In the present invention, the "inorganic particles having an organosilicon structure having a quaternary ammonium group, an imino group or a substituted imino group, and a hydroxyl group (hereinafter also simply referred to as an "organosilicon structure")" is obtained by treating inorganic particles with a silane coupling agent having a quaternary ammonium group, an imino group or a substituted imino group, and a hydroxyl group (hereinafter also simply referred to as a "silane coupling agent") as described above. The "organosilicon structure" as used in the present invention means a structure in which a silicon atom and a carbon atom are bonded. The details of the inorganic particles and the organosilicon structure/silane coupling agent are described later.

In the present invention, the content (% by mass) of the inorganic particles having the organosilicon structure occupied in the ink receiving layer is preferably 50% by mass or more and 98% by mass or less and more preferably 70% by mass or more and 96% by mass or less.

In the present invention, the application amount (g/m²) of the inorganic particles having the organosilicon structure to be applied when forming the ink receiving layer is suitably 8 g/m² or more and 45 g/m² or less.

(1) Inorganic Particles

Examples of the inorganic particles for use in the present invention include, for example, alumina hydrate, fumed alumina, fumed silica, colloidal silica, titanium dioxide, zeolite, kaolin, talc, hydrotalcite, zinc oxide, zinc hydroxide, aluminum silicate, calcium silicate, magnesium silicate, zirconium oxide, zirconium hydroxide, and the like. One or two or more kinds of these inorganic particles can be used as necessary. Among the inorganic particles, the alumina hydrate, the fumed alumina, and the fumed silica capable of forming a porous structure with high ink absorbability are preferably used and particularly the fumed silica is more preferably used.

Examples of the fumed silica for use in the ink receiving layer include Aerosil (manufactured by Nippon Aerosil Co., Ltd.), Reolosil QS type (manufactured by Tokuyama Corporation), and the like.

In the present invention, the specific surface area determined by the BET method of the fumed silica is preferably 50 m²/g or more and 400 m²/g or less and more preferably 200 m²/g or more and 350 m²/g or less.

In the present invention, the fumed silica is suitably used for the coating liquid for ink receiving layer in a state where the fumed silica is dispersed with a dispersant. The particle diameter of the fumed silica in the dispersion state is more suitably 50 nm or more and 300 nm or less. The particle diameter of the fumed silica in the dispersion state can be measured by a dynamic light scattering method.

As the alumina hydrate for use in the ink receiving layer, one represented by General Formula (X): $Al_2O_{3-n}(OH)_{2n}·mH_2O$ can be suitably used (In General Formula (X), n is 0, 1, 2, or 3 and m is 0 or more and 10 or less and preferably 0 or more and 5 or less. m and n are not simultaneously 0.). Since $mH_2O$ represents an aqueous phase which does not participate in the formation of the crystal lattice and which can be disconnected in many cases, m may not be an integer. When the alumina hydrate is heated, m can be 0.

In the present invention, the alumina hydrate can be produced by known methods. Specifically, examples of the methods include a method including hydrolyzing aluminum alkoxide, a method including hydrolyzing sodium aluminate, and a method including adding an aqueous aluminum sulfate solution and aluminum chloride to an aqueous sodium aluminate solution for neutralizing, and the like.

As the crystal structure of the alumina hydrate, an amorphous type, a gibbsite type, and a boehmite type are known according to the heat treatment temperature. The crystal structure of the alumina hydrate can be analyzed by an X-ray diffraction method. In the present invention, among the above, the boehmite type alumina hydrate or the amorphous alumina hydrate is suitable. As specific examples, alumina hydrates described in Japanese Patent Laid-Open Nos. 7-232473, 8-132731, 9-66664, and 9-76628 and the like and Disperal HP14 and HP18 (all manufactured by Sasol) and the like as commercially-available items can be mentioned. One or two or more kinds of these alumina hydrates can be used as necessary.

In the present invention, the specific surface area determined by the BET method of the alumina hydrate is preferably 100 m$^2$/g or more and 200 m$^2$/g or less and more preferably 125 m$^2$/g or more and 175 m$^2$/g or less. Herein, the BET method is a method including causing molecules and ions whose sizes are known to adhere to the surface of a sample, and then measuring the specific surface area of the sample from the adsorption amount. In the present invention, nitrogen gas is used as gas for adsorption to the sample.

As the fumed alumina for use in the ink receiving layer, γ-alumina, α-alumina, δ-alumina, θ-alumina, χ-alumina, and the like can be mentioned. Among the above, γ-alumina is suitably used from the viewpoint of optical density of an image and ink absorbability. As specific examples of the fumed alumina, AEROXIDE; Alu C. Alu130, Alu65 (all manufactured by EVONIK Industries A.G.), and the like can be mentioned.

In the present invention, the specific surface area determined by the BET method of the fumed alumina is preferably 50 m$^2$/g or more and more preferably 80 m$^2$/g or more. The specific surface area is preferably 150 m$^2$/g or less and more preferably 120 m$^2$/g or less.

The average primary particle diameter of the fumed alumina is preferably 5 nm or more and more preferably 11 nm or more. The average primary particle diameter is preferably 30 nm or less and more preferably 15 nm or less.

The alumina hydrate and the fumed alumina are suitably mixed as a water dispersion liquid with the coating liquid for ink receiving layer and acid is suitably used as a dispersing agent therefor. As the acid, sulfonic acid represented by

  General Formula (Y):

is suitably used because the effect of suppressing blurring of an image is obtained (In General Formula (Y), R represents any one of a hydrogen atom, an alkyl group in which the number of carbon atoms is 1 or more and 4 or less, and an alkenyl group in which the number of carbon atoms is 1 or more and 4 or less. R may be substituted with an oxo group, a halogen atom, an alkoxy group, and an acyl group.). The content of the acid is preferably 1.0% by mass or more and 2.0% by mass or less and more preferably 1.3% by mass or more and 1.6% by mass or less based on the total content of the alumina hydrate and the fumed alumina.

(2) Organosilicon Structure/Silane Coupling Agent

In the present invention, the inorganic particles to be contained in the ink receiving layer have an organosilicon structure having a quaternary ammonium group, an imino group or a substituted imino group, and a hydroxyl group. The organosilicon structure can be introduced into the inorganic particles by the use of a silane coupling agent having a quaternary ammonium group, an imino group or a substituted imino group, and a hydroxyl group. The substituted imino group is a group that a hydrogen atom in an imino group is substituted by an atom except for a hydrogen atom or a group of atoms. The substituted imino group is represented by —NR— (R is an atom except for a hydrogen atom or a group of atoms). The organosilicon structure may have the imino group and the substituted imino group. From the viewpoint of dispersibility of the inorganic particles, the organosilicon structure has the quaternary ammonium group, the imino group or the substituted imino group, and the hydroxyl group suitably in the order of the imino group or the substituted imino group, the hydroxyl group, and the quaternary ammonium group or in the order of the hydroxyl group, the imino group or the substituted imino group, and the quaternary ammonium group from the side close to the inorganic particles.

The organosilicon structure is suitably a structure represented by the following general formula (1). The structure represented by General Formula (1) has a monovalent anion as a counter ion. Examples of the monovalent anion include a halogen ion and the like.

[Chem.4]

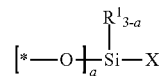

General Formula (1)

A group represented by General Formula (1) is bonded to the surface of the inorganic particles at *. In the formula above, R$^1$ represents an alkyl group or an aryl group having 1 to 8 carbon atoms and X represents a structure represented by the following general formula X, a is 1, 2, or 3.

[Chem.5]

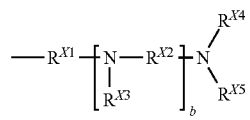

General Formula X

In General Formula X, R$^{X1}$ and R$^{X2}$ each independently represent an alkylene group or an arylene group having 2 to 8 carbon atoms. At least one selected from R$^{X3}$, R$^{X4}$, and R$^{X5}$ represents a structure represented by the following general formula Q and other elements represent a hydrogen atom or an alkyl group or an aryl group having 1 to 8 carbon atoms. b is an integer of 0 to 5. The left end of General Formula X is introduced into X in General Formula (1).

[Chem.6]

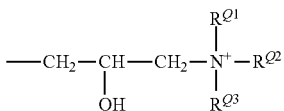

General Formula Q

In General Formula Q, R$^{Q1}$, R$^{Q2}$, and R$^{Q3}$ each independently represent an alkyl group or an aryl group having 1 to 10 carbon atoms. The left end of General Formula Q is introduced into at least one selected from R$^{X3}$, R$^{X4}$, and R$^{X5}$ in General Formula X.

The structure represented by General Formula (1) is in a proportion of preferably 3% by mass or more and 30% by mass or less and more preferably 5% by mass or more and 20% by mass or less in terms of a mass ratio based on the inorganic particles.

In order to obtain the inorganic particles having the structure represented by General Formula (1), a silane coupling agent represented by the following general formula (1)' may be used. The silane coupling agent represented by General Formula (1)' has a monovalent anion as a counter ion. Examples of the monovalent anion include a halogen ion and the like.

[Chem.7]

$$Y_a-\underset{\underset{R^1_{3-a}}{|}}{Si}-X'$$

General Formula (1)

In General Formula (1)', $R^1$ is an alkyl group or an aryl group having 1 to 8 carbon atoms and X represents a structure represented by General Formula X. Y represents a hydrolyzable group, such as a hydroxyl group, a halogen group, an alkoxy group, or an acetoxy group, a is 1, 2, or 3.

In the present invention, the use amount of the silane coupling agent represented by General Formula (1)' is preferably 3% by mass or more and 30% by mass or less and more preferably 5% by mass or more and 20% by mass or less based on the content of the inorganic particles.

The silane coupling agent represented by General Formula (1)' can be obtained by reacting a compound (aminosilane coupling agent) represented by the following general formula (2) and a compound (glycidyl compound having a quaternary ammonium group) represented by the following general formula (3).

[Chem.8]

$$Y_a-\underset{\underset{R^1_{3-a}}{|}}{Si}-R^{X1}-\left[\underset{\underset{R^{X3}}{|}}{N}-R^{X2}\right]_b N\underset{R^{X5}}{\overset{R^{X4}}{\diagup}}$$

General Formula (2)

In General Formula (2), $R^1$ represents an alkyl group or an aryl group having 1 to 8 carbon atoms. Y represents a hydrolyzable group, such as a hydroxyl group, a halogen group, an alkoxy group, or an acetoxy group. $R^{X1}$ and $R^{X2}$ each independently represent an alkylene group or an arylene group having 2 to 8 carbon atoms. At least one selected from $R^{X3}$, $R^{X4}$, and $R^{X5}$ represents a hydrogen atom and other elements represent a hydrogen atom or an alkyl group or an aryl group having 1 to 8 carbon atoms, a is 1, 2, or 3 and b is an integer of 0 to 5.

Specific examples of the compound represented by General Formula (2) include 3-aminopropyltriethoxysilane, 4-aminobutyltriethoxysilane, N-(2-aminoethyl)-3-aminopropyl trimethoxysilane, N-(2-aminoethyl)-3-aminopropylsilanetriol, N-(2-aminoethyl)-3-aminopropylmethyldimethoxysilane, (3-trimethoxy silyl propyl)diethylenetriamine, n-butyl aminopropyltrimethoxysilane, N-ethylaminoisobutyltrimethoxysilane, N-methylaminopropyltrimethoxysilane, N-phenylaminopropyltrimethoxysilane, and the like.

[Chem.9]

$$CH_2\underset{\diagdown O \diagup}{-}CH-CH_2-\underset{\underset{R^{Q3}}{|}}{\overset{\overset{R^{Q1}}{|}}{N^+}}-R^{Q2}$$

General Formula (3)

In General Formula (3), $R^{Q1}$, $R^{Q2}$, and $R^{Q3}$ each independently represent an alkyl group or an aryl group having 1 to 10 carbon atoms. The compound represented by General Formula (3) has a monovalent anion as a counter ion. Examples of the monovalent anion include a halogen ion and the like.

Specific examples of the compound represented by General Formula (3) include glycidyl trimethyl ammonium chloride, glycidyl butyldimethyl ammonium chloride, and the like and can be obtained by an addition reaction of epichlorohydrin and tertiary amine.

In the present invention, the number of the imino groups and/or the substituted imino groups in the structures represented by General Formulae (1) and (1)' is preferably 0.5 times or more and 5.0 times or less and more preferably 1.0 times or more and 3.0 times or less based on the number of the quaternary ammonium groups.

X in General Formulae (1) and (1)' is suitably a structure represented by the following general formula X-1, a structure represented by the following general formula X-2, or a structure represented by the following general formula X-3. The left end of the following general formulae X-1 to X-3 is introduced into X in General Formulae (1) and (1)'.

[Chem.10]

General Formula X-1

In General Formula X-1, at least one selected from $R^{41}$ and $R^{42}$ represents a structure represented by General Formula Q above and other elements represent a hydrogen atom or an alkyl group or an aryl group having 1 to 8 carbon atoms.

[Chem.11]

General Formula X-2

In General Formula X-2, at least one selected from $R^{41}$, $R^{42}$, and $R^{43}$ represents a structure represented by General Formula Q above and other elements represent a hydrogen atom or an alkyl group or an aryl group having 1 to 8 carbon atoms.

[Chem.12]

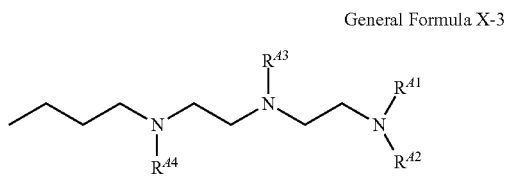

General Formula X-3

In General Formula X-3, at least one selected from $R^{41}$, $R^{42}$, $R^{43}$, and $R^{44}$ represents a structure represented by General Formula Q above and other elements represent a hydrogen atom or an alkyl group or an aryl group having 1 to 8 carbon atoms.

(Binder)

In the present invention, the ink receiving layer contains a binder. In the present invention, the binder refers to a material capable of bonding inorganic particles to form a coating film.

In the present invention, the content of the binder in the ink receiving layer is preferably 50% by mass or less and more preferably 30% by mass or less based on the content of the inorganic particle from the viewpoint of ink absorbability. The ratio is preferably 5.0% by mass or more and more preferably 8.0% by mass or more from the viewpoint of the bonding properties of the ink receiving layers.

Examples of the binder include starch derivatives, such as oxidized starch, esterified starch, and phosphorylated starch; cellulose derivatives, such as carboxymethyl cellulose and hydroxyethyl cellulose, casein, gelatin, soybean protein, polyvinyl alcohol, and derivatives thereof: conjugated polymer latex, such as polyvinylpyrrolidone, maleic anhydride resin, styrene-butadiene copolymers, and methyl methacrylate-butadiene copolymers; acrylic polymer latex, such as acrylic acid ester and methacrylic acid ester polymers, vinyl-based polymer latex, such as ethylenevinyl acetate copolymers; functional group-modified polymer latex of the polymers mentioned above by monomers containing functional groups, such as a carboxyl group; those obtained by cationizing the polymers mentioned above with cationic groups; those obtained by cationizing the surfaces of the polymers mentioned above with cationic surfactants; those obtained by polymerizing monomers constituting the polymers mentioned above in the presence of cationic polyvinyl alcohol so as to disperse the polyvinyl alcohol on the surface of the polymer: those obtained by polymerizing monomers constituting the polymers mentioned above in a suspension/dispersion liquid of cationic colloidal particles so as to disperse the cationic colloidal particles on the surface of the polymer; aqueous binders, such as thermosetting synthetic resin, e.g., melamine resin and urea resin: polymers and copolymers of acrylic acid esters and methacrylic acid esters, such as polymethyl methacrylate; and synthetic resin, such as polyurethane resin, unsaturated polyester resin, vinyl chloride-vinyl acetate copolymers, polyvinyl butyral, and alkyd resin. One or two or more kinds of these binders can be used as necessary.

Among the binders mentioned above, polyvinyl alcohol and polyvinyl alcohol derivatives are particularly suitably used. Examples of the polyvinyl alcohol derivatives include cation-modified polyvinyl alcohol, anion-modified polyvinyl alcohol, silanol-modified polyvinyl alcohol, polyvinyl acetal, and the like. As the cation-modified polyvinyl alcohols, polyvinyl alcohols having primary to tertiary amino groups or a quaternary ammonium group in the main chain or the side chain of polyvinyl alcohol described in Japanese Patent Laid-Open No. 61-10483 are suitable, for example.

The polyvinyl alcohol can be synthesized by saponifying polyvinyl acetate. The degree of saponification of the polyvinyl alcohol is preferably 80% by mol or more and 100% by mol or less and more preferably 85% by mol or more and 98% by mol or less. The degree of saponification is the ratio of the molar number of hydroxyl groups generated by a saponification reaction when polyvinyl acetate is saponified to obtain polyvinyl alcohol, and a value measured by the method described in JIS-K6726 is used in the present invention. The average polymerization degree of the polyvinyl alcohol is preferably 2000 or more and more preferably 2000 or more and 5000 or less. In the present invention, as the average polymerization degree, the viscosity average polymerization degree determined by the method described in JIS-K6726 (1994) is used.

When preparing the coating liquid for ink receiving layer, it is suitable to use polyvinyl alcohol and a polyvinyl alcohol derivative in the form of an aqueous solution. In this case, the solid content of the polyvinyl alcohol and the polyvinyl alcohol derivative in the aqueous solution is suitably 3% by mass or more and 20% by mass or less.

(Crosslinking Agent)

In the present invention, it is suitable for the ink receiving layer to contain a crosslinking agent. Examples of the crosslinking agent include aldehyde compounds, melamine compounds, isocyanate compounds, zirconium compounds, amide compounds, aluminum compounds, boric acids, boric acid salts, and the like. One or two or more kinds of these crosslinking agents can be used as necessary. In particular, when using the polyvinyl alcohol and the polyvinyl alcohol derivative as the binder, boric acid and boric acid salts are suitably used among the crosslinking agents mentioned above.

Examples of the boric acids include orthoboric acid ($H_3BO_3$), metaboric acid, and diboric acid. As the boric acid salt, water-soluble salts of the boric acids mentioned above are suitable. Examples of the boric acid salts include alkali metal salts of boric acids, such as sodium salts and potassium salts of boric acids; alkaline earth metal salts of boric acids, such as magnesium salts and calcium salts of boric acids; ammonium salts of boric acids; and the like. Among the above, the use of the orthoboric acid is suitable from the viewpoint of stability with time of the coating liquid and the effect of suppressing the occurrence of cracking.

The use amount of the crosslinking agent can be adjusted as appropriate according to the production conditions and the like. In the present invention, the content of the crosslinking agent in the ink receiving layer is preferably 1.0% by mass or more and 50% by mass or less and more preferably 5% by mass or more and 40% by mass or less based on the content of the binder.

When the binder is polyvinyl alcohol and the crosslinking agent is at least one kind selected from the boric acids and the boric acid salts, the total content of the boric acid and the boric acid salt is suitably 5% by mass or more and 30% by mass or less based on the content of the polyvinyl alcohol in the ink receiving layer.

(Other Additives)

In the present invention, the ink receiving layer may contain other additives other than the substances described above. Specific examples of the additives include pH adjusters, thickeners, fluidity modifiers, antifoaming agents, foam inhibitors, surfactants, mold release agents, penetrants, color pigments, color dyes, fluorescent brightening agents, ultraviolet absorbers, antioxidants, antiseptics, antifungal agents, water resistant additives, dye-fixing agents, curing agents, weather resistant materials, and the like.

In particular, in the present invention, in order to increase the moisture resistance from the viewpoint of storage of a recording medium to be obtained, it is suitable for the ink receiving layer to further contain a water-soluble polyvalent metal compound or cationic resin particles.

(1) Water-Soluble Polyvalent Metal Compound

Examples of the water-soluble polyvalent metal compound include calcium, barium, manganese, copper, cobalt, nickel, aluminum, iron, zinc, zirconium, titanium, chromium, magnesium, tungsten, and molybdenum and the water-soluble polyvalent metal compound can be used as a water-soluble salt of the metals. Specific examples include, for example, calcium acetate, calcium chloride, calcium formate, calcium sulfate, calcium lactate, barium acetate, barium sulfate, barium phosphate, manganese chloride, manganese acetate, manganese formate dihydrate, manganese chloride, manganese acetate, manganese formate dihydrate, manganese ammonium sulfate hexahydrate, cupric chloride, ammonium copper(II) chloride dihydrate, copper sulfate, cobalt chloride, cobalt thiocyanate, cobalt sulfate, nickel sulfate hexahydrate, nickel chloride hexahydrate, nickel acetate tetrahydrate, nickel ammonium sulfate hexahydrate, nickel amidosulfate tetrahydrate, aluminum sulfate, aluminum sulfite, aluminum thiosulfate, polyaluminum chloride, aluminum nitrate nonahydrate, aluminum chloride hexahydrate, aluminum lactate, ferrous bromide, ferrous chloride, ferric chloride, ferrous sulfate, ferric sulfate, zinc bromide, zinc chloride, zinc nitrate hexahydrate, zinc sulfate, zirconium acetate, zirconium nitrate, basic zirconium carbonate, zirconium hydroxide, zirconium-ammonium carbonate, zirconium-potassium carbonate, zirconium sulfate, zirconium fluoride, zirconium chloride, zirconium chloride octahydrate, zirconium oxychloride, zirconium hydroxychloride, titanium chloride, titanium sulfate, chromium acetate, chromium sulfate, magnesium sulfate, magnesium chloride hexahydrate, magnesium citrate nonahydrate, magnesium lactate, sodium phosphotungstate, sodium tungsten citrate, 12-tungstophosphate n-hydrate, 12-tungstosilicate hexacosahydrate, molybdenum chloride, 12-molybdophosphate n-hydrate, and the like. Among the above, the aluminium compound or the zirconium compound is suitable, and the polyaluminium chloride or the zirconium acetate is particularly suitable.

In the present invention, the content of the water-soluble polyvalent metal compound in the ink receiving layer is preferably 1% by mass or more and 10% by mass or less and more preferably 1% by mass or more and 5% by mass or less based on the content of the inorganic particles.

(2) Cationic Resin Particles

Examples of the cationic resin particles include conjugated diene resin particles, such as a styrene-butadiene copolymer and a methyl methacrylate-butadiene copolymer: acrylic resin particles, such as polymers or copolymers of acrylic acid esters and methacrylic acid esters and polymers or copolymers of acrylic acids or methacrylic acids; those obtained by cationizing vinyl resin particles, such as an ethylene vinyl acetate copolymer, those obtained by cationizing the surface of resin particles using a cationic surfactant, and the like. Among the above, the resin particles containing the styrene-acryl copolymer are suitable.

In the present invention, the content of the cationic resin in the ink receiving layer is preferably 1% by mass or more and 10% by mass less and more preferably 1% by mass or more and 5% by mass or less based on the content of the inorganic particles.

<Undercoat Layer>

In the present invention, an undercoat layer may be provided between the base material and the ink receiving layer for the purpose of increasing the adhesiveness between the base material and the ink receiving layer. The undercoat layer suitably contains a water-soluble polyester resin, gelatin, polyvinyl alcohol, and the like. The film thickness of the undercoat layer is suitably 0.01 µm or more and 5 µm or less.

<Back Coat Layer>

In the present invention, a back coat layer may be provided on a surface opposite to the surface on which the ink receiving layer is provided of the base material for the purpose of increasing the handling properties, the conveyance aptitude, and the conveyance scratch resistance in continuation printing in the case of loading a large number of sheets. The back coat layer suitably contains a white pigment, a binder, and the like. The film thickness of the back coat layer is set in such a manner that the dry application amount is 1 $g/m^2$ or more and 25 $g/m^2$ or less.

Method for Manufacturing Recording Medium

In the present invention, a method for manufacturing the recording medium is not particularly limited and a manufacturing method is suitable which includes a process of preparing a coating liquid for ink receiving layer and a process of applying the coating liquid for ink receiving layer to the base material. Hereinafter, the method for manufacturing the recording medium is described.

(Method for Producing Base Material)

In the present invention, as a method for producing a base paper, a generally used paper-making method can be applied. Examples of the paper-making machine include Fourdrinier paper machines, cylinder paper machines, drum paper machines, twin wire paper machines, and the like. In order to improve the surface smoothness of the base paper, surface treatment may be performed by applying heat and pressure during the paper-making process or after the paper-making process. Specific examples of the surface treatment methods include calendar treatment, such as machine calendar and super calendar.

Examples of a method for providing a resin layer on the base paper, i.e., a method for covering the base paper with resin, include a melt extrusion method, wet lamination, dry lamination, and the like. Among the above, the melt extrusion method including performing extrusion coating of molten resin to one surface or both surfaces of the base paper is suitable. For example, a method including bringing a base paper, which is conveyed, and a resin, which is extruded from an extrusion die, into contact with each other at a nip point between a nip roller and a cooling roller, and then press-bonding the base paper and the resin at the nip to thereby laminate a resin layer onto the base paper (hereinafter also referred to as an extrusion coating method) is widely adopted. When providing the resin layer by the melt extrusion method, pretreatment may be performed in such a manner that the adhesion of the base paper and the resin layer becomes stronger. Examples of the pretreatment include acid etching treatment with a sulfuric acid-chromic acid mixed liquid, flame treatment with a gas flame, ultraviolet-ray irradiation treatment, corona discharge treatment, glow discharge treatment, anchor coat treatment with alkyl titanate, and the like, for example. Among the above, the corona discharge treatment is suitable. When blending a white pigment in the resin layer, the base paper may be covered with a mixture of the resin and the white pigment.

<Method for Forming Ink Receiving Layer>

In the recording medium of the present invention, as a method for forming the ink receiving layer on the base material, the following method can be mentioned, for example. First, a coating liquid for ink receiving layer is prepared. Then, by applying the coating liquid onto the base material, and then drying the resultant substance, the recording medium of the present invention can be obtained. As a method including applying the coating liquid, a curtain coater, a coater using an extrusion system, a coater using a slide hopper system, and the like can be used. During the application, the coating liquid may be warmed. Examples of a drying method after the application include methods using hot air dryers, such as a linear tunnel dryer, an arch dryer, an air loop dryer, and a sine curve air float dryer, methods using a dryer utilizing infrared rays or microwaves, and the like.

EXAMPLES

Hereinafter, the present invention is described in more detail with reference to EXAMPLEs and COMPARATIVE EXAMPLEs. The present invention is not limited by the following examples without diverting from the scope of the present invention. In the following examples, the term "part(s)" is based on mass unless otherwise particularly specified.

<Production of Base Material>

80 parts of LBKP having a Canadian Standard Freeness of 450 mLCSF, 20 parts of NBKP having a Canadian Standard Freeness of 480 mLCSF, 0.60 part of cationized starch, 10 parts of heavy calcium carbonate, 15 parts of light calcium carbonate, 0.10 part of alkyl ketene dimer, and 0.030 part of cationic polyacrylamide were mixed, and then water was added in such a manner that the solid content was 3.0% by mass to thereby obtain a paper stuff. Subsequently, the paper stuff was formed into paper with a Fourdrinier paper machine, and then subjected to three-stage wet pressing, followed by drying with a multi-cylinder dryer. Thereafter, the resultant paper was impregnated with an aqueous oxidized starch solution in such a manner that the solid content after the drying was 1.0 g/m² using a size press apparatus, and then dried. Furthermore, the resultant paper was subjected to finishing treatment with a machine calendar to produce a base paper having a basis weight of 170 g/m², a stockigt sizing degree of 100 seconds, an air permeability of 50 seconds, a Bekk smoothness of 30 seconds, a Gurley stiffness of 11.0 mN, and a film thickness of 100 μm. Subsequently, a resin composition containing 70 parts of low-density polyethylene, 20 parts of high-density polyethylene, and 10 parts of titanium oxide was applied onto one surface of the base paper in such a manner that the dry application amount was 25 g/m². This surface was used as the front surface. Furthermore, the low-density polyethylene was applied to the other surface of the base paper, whereby a base material was obtained. When the arithmetic average roughness Ra (Measurement length: 2.5 mm, Cutoff value: 0.8 mm) defined by JIS B 0601:2001 of the front surface of the obtained base material was measured to be 0.2 μm.

<Synthesis of Silane Coupling Agent>

A silane coupling agent was synthesized by a method described below. The structure of the silane coupling agent after the synthesis was identified using a nuclear magnetic resonance spectroscopic method ($^1$H-NMR and $^{13}$C-NMR). Using Advance500 CRYOSYSTEM (manufactured by BRUKER) as the device for the nuclear magnetic resonance spectroscopic method, moisture was distilled from an aqueous solution of each silane coupling agent, under reduced pressure, and then the resultant substance was dissolved again with heavy water to produce a sample. By the comparison with an aminosilane coupling agent and a glycidyl compound serving as the raw materials, the peak (3.5 to 4.0 ppm) showing the existence of a hydroxyl group generated after the reaction was confirmed using $^1$H-NMR. Moreover, by the comparison with an aminosilane coupling agent and a glycidyl compound serving as the raw materials, the peak (63 to 70 ppm) showing the existence of a hydroxyl group generated after the reaction was confirmed using $^{13}$C-NMR.

(Synthesis of Silane Coupling Agent A-1)

In 161 parts of ion exchange water, 22.2 parts of N-(2-aminoethyl)-3-aminopropyl trimethoxysilane was dissolved, and then 19.0 parts of an aqueous solution of glycidyl trimethyl ammonium chloride (manufactured by Sakamoto Yakuhin kogyo Co., Ltd., SY-GTA80) was added under stirring. The stirring was further performed at 60° C. for 1 hour, and then heating was stopped. Then, the resultant substance was allowed to stand still until the temperature reached room temperature, whereby an aqueous solution of a silane coupling agent A-1 with a solid content concentration of 17.8% was obtained.

[Chem.13]

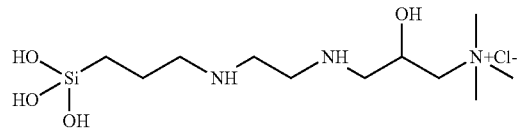

A-1

(Synthesis of Silane Coupling Agent A-2)

In 139.8 parts of ion exchange water, 13.3 parts of N-(2-aminoethyl)-3-aminopropyl trimethoxysilane was dissolved, and then 22.7 parts of an aqueous solution of glycidyl trimethyl ammonium chloride (manufactured by Sakamoto Yakuhin kogyo Co., Ltd., SY-GTA80) was added under stirring. The stirring was further performed at 60° C. for 1 hour, and then heating was stopped. Then, the resultant substance was allowed to stand still until the temperature reached room temperature, whereby an aqueous solution of a silane coupling agent A-2 with a solid content concentration of 18.4% was obtained.

[Chem.14

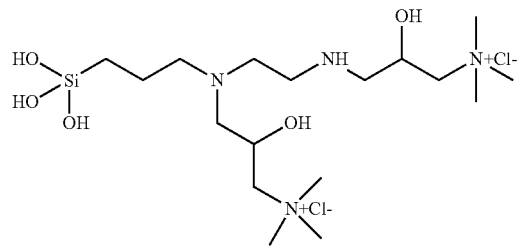

A-2

(Synthesis of Silane Coupling Agent A-3)

In 152.5 parts of ion exchange water, 11.2 parts of N-(2-aminoethyl)-3-aminopropyl trimethoxysilane was dissolved, and then 28.4 parts of an aqueous solution of glycidyl trimethyl ammonium chloride (manufactured by Sakamoto Yakuhin kogyo Co., Ltd., SY-GTA80) was added under stirring. The stirring was further performed at 60° C. for 1 hour, and then heating was stopped. Then, the resultant substance was allowed to stand still until the temperature reached room temperature, whereby an aqueous solution of a silane coupling agent A-3 with a solid content concentration of 18.8% was obtained.

[Chem.15]

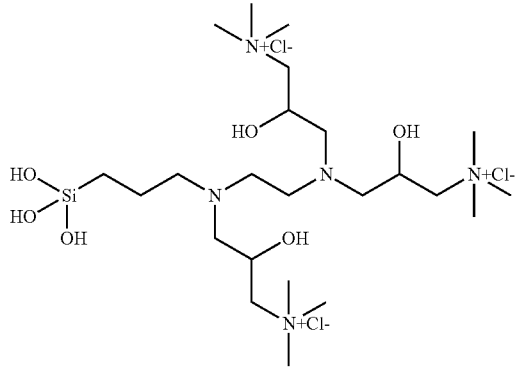

A-3

(Synthesis of Silane Coupling Agent B-1)

In 160.9 parts of ion exchange water, 22.2 parts of 3-aminopropyl triethoxysilane was dissolved, and then 19.0 parts of an aqueous solution of glycidyl trimethyl ammonium chloride (manufactured by Sakamoto Yakuhin kogyo Co., Ltd., SY-GTA80) was added under stirring. The stirring was further performed at 60° C. for 1 hour, and then heating was stopped. Then, the resultant substance was allowed to stand still until the temperature reached room temperature, whereby an aqueous solution of a silane coupling agent B-1 with a solid content concentration of 15.5% was obtained.

[Chem. 16]

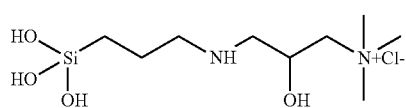

B-1

(Synthesis of Silane Coupling Agent B-2)

In 139.7 parts of ion exchange water, 13.3 parts of 3-aminopropyl triethoxysilane was dissolved, and then 22.7 parts of an aqueous solution of glycidyl trimethyl ammonium chloride (manufactured by Sakamoto Yakuhin kogyo Co., Ltd., SY-GTA80) was added under stirring. The stirring was further performed at 60° C. for 1 hour, and then heating was stopped. Then, the resultant substance was allowed to stand still until the temperature reached room temperature, whereby an aqueous solution of a silane coupling agent B-2 with a solid content concentration of 16.8% was obtained.

[Chem. 17]

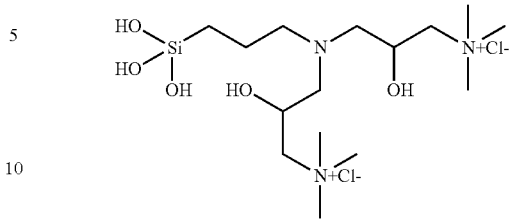

B-2

(Synthesis of Silane Coupling Agent C-1)

In 178.2 parts of ion exchange water, 26.5 parts of (3-trimethoxysilylpropyl)diethylenetriamine was dissolved, and then 18.9 parts of an aqueous solution of glycidyl trimethyl ammonium chloride (manufactured by Sakamoto Yakuhin kogyo Co., Ltd., SY-GTA80) was added under stirring. The stirring was further performed at 60° C. for 1 hour, and then heating was stopped. Then, the resultant substance was allowed to stand still until the temperature reached room temperature, whereby an aqueous solution of a silane coupling agent C-1 with a solid content concentration of 18% was obtained.

[Chem. 18]

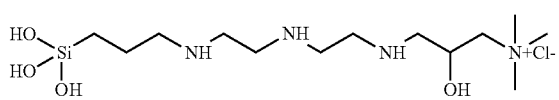

C-1

(Synthesis of Silane Coupling Agent D-1)

In 162 parts of ion exchange water, 22.2 parts of N-(2-aminoethyl)-3-aminopropyltrimethoxysilane was dissolved, and then 24.2 parts of an 80% aqueous solution of glycidyl triethyl ammonium chloride was added under stirring. The stirring was further performed at 60° C. for 1 hour, and then heating was stopped. Then, the resultant substance was allowed to stand still until the temperature reached room temperature, whereby an aqueous solution of a silane coupling agent D-1 with a solid content concentration of 18% was obtained.

[Chem. 19]

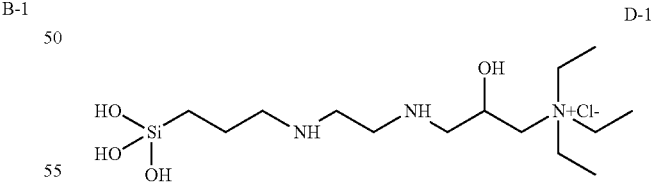

D-1

(Synthesis of Silane Coupling Agent E-1)

In 193.2 parts of ion exchange water, 22.2 parts of N-(2-aminoethyl)-3-aminopropyltrimethoxysilane was dissolved, and then 34.7 parts of an 80% aqueous solution of glycidyl tributyl ammonium chloride was added under stirring. The stirring was further performed at 60° C. for 1 hour, and then heating was stopped. Then, the resultant substance was allowed to stand still until the temperature reached room temperature, whereby an aqueous solution of a silane coupling agent E-1 with a solid content concentration of 18% was obtained.

[Chem. 20]

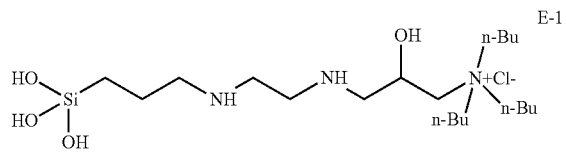

Example 1-1

(1) Preparation of Inorganic Particle Dispersion Liquid 1

To 172.5 parts of ion exchange water, 26.6 parts (10 parts by mass in terms of solid content based on 100 parts by mass of fumed silica) of the silane coupling agent A-1 and 3.42 parts (0.72 part by mass based on 100 parts by mass of fumed silica) of an aqueous 10% methanesulfonic acid solution were added. 47.4 parts of fumed silica AEROSIL 300 (manufactured by EVONIK Industries A.G.) was added in a small amount while stirring the aqueous solution with a T.K. homomixer MARK II 2.5 (manufactured by Tokusyu Kika Kogyo Co., Ltd.) under the rotation conditions of 5000 rpm. Furthermore, the resultant aqueous solution was treated under the rotation conditions of 10000 rpm for 30 minutes by CLEARMIX (manufactured by M Technique Co., Ltd.), whereby an inorganic particle dispersion liquid 1 with a solid content of 20% by mass was prepared.

(2) Preparation of Binder Solution

Polyvinyl alcohol PVA 235 (manufactured by Kuraray Co., Ltd., Viscosity average polymerization degree: 3500, Saponification degree: 88% by mol) was dissolved in ion exchange water to prepare a binder solution with a solid content of 8.0% by mass.

(3) Preparation of Coating Liquid for Ink Receiving Layer

The binder solution was mixed in such a manner that the solid content in the binder solution was 23.0 parts based on 100 parts of the solid content of the fumed silica contained in the inorganic particle dispersion liquid 1 to obtain a mixed solution. Subsequently, an aqueous orthoboric acid solution (Solid content of 5% by mass) which was a crosslinking agent was mixed in such a manner as to have an amount of 3 parts in terms of solid content based on 100 parts of the solid content of the fumed silica contained in the obtained mixed solution, and further ion exchange water was added as appropriate, whereby a coating liquid for ink receiving layer having a total solid content concentration of 15% was obtained.

(4) Production of Recording Medium

The coating liquid for ink receiving layer prepared above was applied onto the base material obtained above. The coating liquid was applied in such a manner that the dry application amount was 26 g/m² at this time. Furthermore, after the application, the resultant substance was dried with 90° C. hot air to obtain a recording medium of EXAMPLE 1-1. The arithmetic average roughness Ra (Measurement length: 2.5 mm, Cutoff value: 0.8 mm) defined by JIS B 0601:2001 of the surface of the obtained recording medium was measured to be 0.1 m.

Examples 1-2 to 1-8

Recording media of EXAMPLEs 1-2 to 1-8 were obtained in the same manner as in EXAMPLE 1-1, except changing the silane coupling agent A-1 to silane coupling agents shown in the following table 1 and adding methanesulfonic acid in such a manner that the pH of the dispersion liquid was 5 to 6 in the preparation of the inorganic particle dispersion liquid 1 in EXAMPLE 1-1.

Examples 1-9 to 1-12

Recording media of EXAMPLEs 1-9 to 1-12 were obtained in the same manner as in EXAMPLE 1-1, except changing the use amount of the silane coupling agent A-1 (in terms of solid content based on 100 parts by mass fumed silica) to 5 parts. 7 parts. 12 parts, and 15 parts, respectively, in EXAMPLE 1-1.

Comparative Example 1-1

An recording medium of COMPARATIVE EXAMPLE 1-1 was obtained in the same manner as in EXAMPLE 1-1, except changing the inorganic particle dispersion liquid 1 to an inorganic particle dispersion liquid 2 described below in EXAMPLE 1-1.

(Preparation of Inorganic Particle Dispersion Liquid 2)

To 195 parts of ion exchange water, 5 parts (5 parts by mass in terms of solid content based on 100 parts by mass of fumed silica) of p-DADMAC (manufactured by Daiichi Kogyo Seiyaku Co., Ltd., SHALLOL DC902-P, Solid content of 50% by mass) was added. 50 parts of fumed silica AEROSIL 300 (manufactured by EVONIK Industries A.G.) was added in a small amount while stirring the aqueous solution with a T.K. homomixer MARK II 2.5 (manufactured by Tokusyu Kika Kogyo Co., Ltd.) under the rotation conditions of 5000 rpm. Furthermore, the resultant aqueous solution was treated under the rotation conditions of 10000 rpm for 30 minutes by CLEARMIX (manufactured by M Technique Co., Ltd.), whereby an inorganic particle dispersion liquid 2 with a solid content of 21% by mass was prepared.

Comparative Example 1-2

A recording medium of COMPARATIVE EXAMPLE 1-2 was obtained in the same manner as in EXAMPLE 1-1, except changing the silane coupling agent to N-trimethoxysilylpropyl-N,N,N-trimethyl ammonium chloride.

Comparative Example 1-3

A recording medium of COMPARATIVE EXAMPLE 1-3 was obtained in the same manner as in EXAMPLE 1-1, except changing the silane coupling agent to a silane coupling agent having a structure of the following formula F-1.

[Chem. 21]

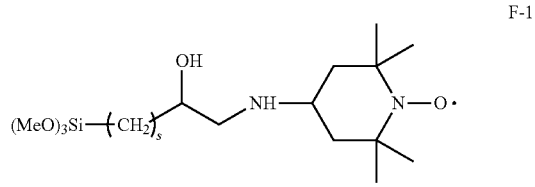

Comparative Example 1-4

A recording medium of COMPARATIVE EXAMPLE 1-4 was obtained in the same manner as in EXAMPLE 1-1, except changing the silane coupling agent A-1 in EXAMPLE 1-1 to 5 parts in terms of solid content of N-trimethoxysilylpropyl-N,N,N-trimethyl ammonium chloride and 5 parts of the silane coupling agent represented by F-1 above.

Evaluation 1

(Evaluation of Color Development Properties of Image to be Obtained)

On each recording medium obtained in each of EXAMPLEs 1-1 to 1-12 and COMPARATIVE EXAMPLEs 1-1 to 1-4, a 2.5 cm×2.5 cm black solid image (image with a recording duty of 100%) was recorded in a mode of "Photo paper, Glossy gold, No color correction" using an ink jet recording apparatus PIXUS MG7130 (manufactured by CANON KABUSHIKI KAISHA) to which an ink cartridge BCI-351 (manufactured by CANON KABUSHIKI KAISHA) was attached. As the recording conditions, the temperature was set to 23° C., and the relative humidity was set to 50%. The optical density of the obtained image was measured using an optical reflection densitometer 530 spectral densitometer (manufactured by X-Rite). The color development properties of the image were evaluated from the obtained optical density values. When the optical density value is larger, the color development properties of the image are higher. The evaluation criteria are as follows. The evaluation results are shown in Table 1.

A: Optical density was 2.35 or more.
B: Optical density was 2.25 or more and less than 2.35.
C: Optical density was 2.15 or more and less than 2.25.
D: Optical density was 2.05 or more and less than 2.15.
E: Optical density was less than 2.05.

(Evaluation of Ink Absorbability)

On each recording medium obtained above, a 2.5 cm×2.5 cm cyan solid image (image with a recording duty of 100%) was recorded in a mode of "Photo paper, Glossy gold, No color correction" using the ink jet recording apparatus. The recorded cyan image was observed under fluorescent light, and then the color tone of regular reflected light was visually checked. The evaluation criteria are as follows. The evaluation results are shown in Table 1.

A: The reflected light looked white.
B: The reflected light slightly looked pink.
C: The reflected light looked faint pink.
D: The reflected light looked intense pink.

(Evaluation of Cracking in Ink Receiving Layer)

Each recording medium obtained above was visually observed, and the cracking in the ink receiving layer was evaluated. The evaluation criteria are as follows. The evaluation results are shown in Table 1.

A: Cracking did not occur in the ink receiving layer or the cracking slightly occurred.
B: Cracking occurred in the ink receiving layer but was negligible.

TABLE 1

Production conditions and evaluation results of recording media

| | | Silane coupling agent | | Evaluation results | | |
|---|---|---|---|---|---|---|
| Ex. No. | Inorganic particles | Type | Use amount*1 (Part) | Color development properties | Ink absorbability | Cracking in ink receiving layer |
| Ex. 1-1 | AEROSIL 300 | A-1 | 10 | A | A | A |
| Ex. 1-2 | AEROSIL 300 | A-2 | 10 | B | B | A |
| Ex. 1-3 | AEROSIL 300 | A-3 | 10 | B | C | A |
| Ex. 1-4 | AEROSIL 300 | B-1 | 10 | B | A | A |
| Ex. 1-5 | AEROSIL 300 | B-2 | 10 | C | B | A |
| Ex. 1-6 | AEROSIL 300 | C-1 | 10 | A | A | A |
| Ex. 1-7 | AEROSIL 300 | D-1 | 10 | A | A | A |
| Ex. 1-8 | AEROSIL 300 | E-1 | 10 | A | A | A |
| Ex. 1-9 | AEROSIL 300 | A-1 | 5 | C | A | A |
| Ex. 1-10 | AEROSIL 300 | A-1 | 7 | B | A | A |
| Ex. 1-11 | AEROSIL 300 | A-1 | 12 | A | B | A |
| Ex. 1-12 | AEROSIL 300 | A-1 | 15 | C | C | A |
| Comp. Ex. 1-1 | AEROSIL 300 | p-DADMAC | 5 | C | D | B |
| Comp. Ex. 1-2 | AEROSIL 300 | N-trimethoxysilylpropyl-N,N,N-trimethyl ammonium chloride | 10 | D | C | B |
| Comp. Ex. 1-3 | AEROSIL 300 | F-1 | 5 | D | C | B |
| Comp. Ex. 1-4 | AEROSIL 300 | N-trimethoxysilylpropyl-N,N,N-trimethyl ammonium chloride/F-1 | 5/5 | C | C | B |

*1Solid content amount based on 100 parts by mass of fumed silica

Example 2-1

(1) Preparation of Coating Liquid for Ink Receiving Layer

Based on 100 parts of the solid content of the fumed silica contained in the inorganic particle dispersion liquid 1, 1 part of zirconium acetate (manufactured by Chemical Point UG, Solid content concentration of 22%) and 3 parts of cationic styrene-acryl emulsion B270D (manufactured by BASF. Solid content concentration of 31.6%) were mixed in such a manner that the solid content in the binder solution was 23.0 parts to obtain a mixed solution. Subsequently, an aqueous orthoboric acid solution (Solid content of 5% by mass) which was a crosslinking agent was mixed in such a manner as to have an amount of 3 parts in terms of solid content based on 100 parts of the solid content of the fumed silica contained in the obtained mixed solution, and further ion exchange water was added as appropriate, whereby a coating liquid for ink receiving layer having a total solid content concentration of 15% was obtained.

(2) Production of Recording Medium

The coating liquid for ink receiving layer prepared above was applied onto the base material obtained above. The coating liquid was applied in such a manner that the dry application amount was 26 g/m$^2$ at this time. Furthermore, after the application, the resultant substance was dried with 90° C. hot air to obtain a recording medium.

Examples 2-2 to 2-4

Recording media of EXAMPLEs 2-2 to 2-4 were obtained in the same manner as in EXAMPLE 2-1, except changing the use amount of the zirconium acetate (in terms of solid content based on 100 parts by mass of fumed silica) to 3 parts, 5 parts, and 10 parts, respectively, in EXAMPLE 2-1.

Example 2-5

A recording medium of EXAMPLE 2-5 was obtained in the same manner as in EXAMPLE 2-1, except changing the zirconium acetate to polyaluminium chloride in EXAMPLE 2-1.

Examples 2-6 to 2-8

Recording media of EXAMPLEs 2-6 to 2-8 were obtained in the same manner as in EXAMPLE 2-5, except changing the use amount of the polyaluminium chloride (in terms of solid content based on 100 parts by mass of fumed silica) to 3 parts, 5 parts, and 10 parts, respectively, in EXAMPLE 2-5.

Examples 2-9 to 2-11

Recording media of EXAMPLEs 2-9 to 2-11 were obtained in the same manner as in EXAMPLE 2-1, except changing the use amount of the cationic styrene-acryl emulsion (in terms of solid content based on 100 parts by mass of fumed silica) to 1 part, 5 parts, and 10 parts, respectively, in EXAMPLE 2-1.

Examples 2-12 and 2-13

Recording media of EXAMPLEs 2-12 and 2-13 were obtained in the same manner as in EXAMPLE 2-1, except changing both the use amount of the zirconium acetate and the use amount of the cationic styrene-acryl emulsion (in terms of solid content based on 100 parts by mass of fumed silica) to 5 parts and 10 parts in EXAMPLE 2-1.

Example 2-14

A recording medium of EXAMPLE 2-17 was obtained in the same manner as in EXAMPLE 2-1, except not using zirconium acetate in EXAMPLE 2-1.

Examples 2-15 and 2-16

Recording media of EXAMPLEs 2-15 and 2-16 were obtained in the same manner as in EXAMPLE 2-14, except changing the use amount of the zirconium acetate (in terms of solid content based on 100 parts by mass of fumed silica) to 3 parts and 5 parts, respectively, in EXAMPLE 2-14.

Example 2-17

A recording medium of EXAMPLE 2-17 was obtained in the same manner as in EXAMPLE 2-1, except not using zirconium acetate and changing the use amount of the cationic styrene-acryl emulsion (in terms of solid content based on 100 parts by mass of fumed silica) to 1 part in EXAMPLE 2-1.

Examples 2-18 and 2-19

Recording media of EXAMPLEs 2-18 and 2-19 were obtained in the same manner as in EXAMPLE 2-17, except changing the use amount of the cationic styrene-acryl emulsion (in terms of solid content based on 100 parts by mass of fumed silica) to 3 parts and 5 parts, respectively, in EXAMPLE 2-17.

Example 2-20

A recording medium of EXAMPLE 2-20 was obtained in the same manner as in EXAMPLE 2-1, except changing "1 part of zirconium acetate" to "1 part of zirconium acetate and 1 part of polyaluminium chloride" in EXAMPLE 2-1.

Examples 2-21 to 2-23

Recording media of EXAMPLEs 2-21 to 2-23 were obtained in the same manner as in EXAMPLE 2-19, except changing the cationic styrene-acryl emulsion to acryl emulsion, vinyl chloride-acryl emulsion, and polyester-based polyurethane emulsion, respectively, in EXAMPLE 2-19.

Examples 2-24 to 2-28

Recording media of EXAMPLEs 2-24 to 2-28 were obtained in the same manner as in EXAMPLE 2-1, except changing the silane coupling agent A-1 to the silane coupling agents A-2 to C-1, respectively, in EXAMPLE 2-1.

Examples 2-29 to 2-32

Recording media of EXAMPLEs 2-29 to 2-32 were obtained in the same manner as in EXAMPLE 2-1, except changing the use amount of the silane coupling agent A-1 (in terms of solid content based on 100 parts by mass of fumed silica) to 5 part, 7 parts, 12 parts, and 15 parts, respectively, in EXAMPLE 2-1.

Evaluation 2

The "Evaluation of color development properties of image to be obtained", "Evaluation of ink absorbability", and "Evaluation of cracking in ink receiving layer" were evaluated in the same manner as in the evaluation described above.

(Evaluation of Moisture Resistance of Image to be Obtained)

On each recording medium obtained above, a black cyan solid image (image with a recording duty of 100%) was recorded in a mode of "Photo paper, Glossy gold. No color correction" using the ink jet recording apparatus. The obtained image was stored for 1 week in an environment of Temperature: 25° C., and Relative humidity: 85%. The image after the storage was visually checked and evaluated based on the following evaluation criteria. The evaluation results are shown in Table 2.

A: Blurring was hardly able to be visually recognized.

B: Blurring was able to be visually recognized but was inconspicuous.

TABLE 2

| | Color development properties of image to be obtained | Ink absorbability | Cracking in ink receiving layer | Moisture resistance of image to be obtained |
|---|---|---|---|---|
| Ex. 2-1 | A | A | A | A |
| Ex. 2-2 | A | A | A | A |
| Ex. 2-3 | B | B | A | A |
| Ex. 2-4 | C | B | B | A |
| Ex. 2-5 | A | A | A | A |
| Ex. 2-6 | A | A | A | A |
| Ex. 2-7 | B | B | A | A |
| Ex. 2-8 | C | B | B | A |
| Ex. 2-9 | A | A | A | B |
| Ex. 2-10 | B | B | A | A |
| Ex. 2-11 | C | B | A | A |
| Ex. 2-12 | C | B | A | A |
| Ex. 2-13 | C | C | B | A |
| Ex. 2-14 | A | A | A | B |
| Ex. 2-15 | A | A | A | B |
| Ex. 2-16 | B | A | A | A |
| Ex. 2-17 | A | A | A | B |
| Ex. 2-18 | A | A | A | B |
| Ex. 2-19 | B | A | A | A |
| Ex. 2-20 | A | A | A | A |
| Ex. 2-21 | B | A | A | B |
| Ex. 2-22 | B | A | A | B |
| Ex. 2-23 | B | A | A | B |
| Ex. 2-24 | B | B | A | A |
| Ex. 2-25 | B | C | A | A |
| Ex. 2-26 | B | A | A | A |
| Ex. 2-27 | C | B | A | A |
| Ex. 2-28 | A | A | A | A |
| Ex. 2-29 | C | A | A | A |
| Ex. 2-30 | B | A | A | A |
| Ex. 2-31 | A | B | A | A |
| Ex. 2-32 | C | C | A | A |

Examples 3-1 to 3-4

Recording media of EXAMPLEs 3-1 to 3-4 were obtained in the same manner as in EXAMPLE 1-1, except changing the arithmetic average roughness Ra defined by JIS B 0601:2001 of a base material to 1.5, 3.0, 4.5, and 6.0, respectively, in EXAMPLE 1-1.

Evaluation 3

(Evaluation of Gloss Unevenness)

On each recording medium obtained above, a 2.5 cm×2.5 cm black solid image (image with a recording duty of 100%) was recorded in a mode of "Photo paper, Glossy gold, No color correction" using the ink jet recording apparatus, the 60° glossiness of each of the black solid image and a non-printed portion was measured, and then the gloss difference was visually judged. The results are shown in Table 3.

TABLE 3

| Ex. No. | Ra of base material surface (μm) | Evaluation of gloss unevenness |
|---|---|---|
| Ex. 3-1 | 1.5 | A |
| Ex. 3-2 | 3.0 | A |
| Ex. 3-3 | 4.5 | B |
| Ex. 3-4 | 6.0 | C |

A: The gloss difference was hardly recognized.
B: The gloss difference was slightly recognized.
C: The gloss difference was recognized.

Examples 4-1 to 4-6

Recording media of EXAMPLEs 4-1 to 4-6 were obtained in the same manner as in EXAMPLE 1-1, except changing the arithmetic average roughness Ra defined by JIS B 0601:2001 of a base material to 0.8, 1.5, 2.0, 2.5, 3.0, and 6.0, respectively, in EXAMPLE 1-1.

Evaluation 4

(Evaluation of Visibility of Damages of Surface of Recording Medium)

On each recording medium obtained above, a 2.5 cm×2.5 cm black solid image (image with a recording duty of 100%) was recorded in a mode of "Photo paper, Glossy gold, No color correction" using the ink jet recording apparatus. After the black solid image was recorded, the black solid image was dried in an environment of Temperature: 23° C., and Relative humidity: 50% for 24 hours. Thereafter, the recording surfaces were overlapped with each other, and then repeatedly rubbed against each other (to the front and to the rear by about 3 cm) 50 times under a load of 1.5 g/m$^2$. Then, the recorded surfaces were visually observed, and then evaluated based on the following criteria.

TABLE 4

| Ex. No. | Ra of recording medium surface (μm) | Evaluation of visibility of damages |
|---|---|---|
| Ex. 4-1 | 0.8 | A |
| Ex. 4-2 | 1.5 | A |
| Ex. 4-3 | 2.0 | A |
| Ex. 4-4 | 2.5 | A |
| Ex. 4-5 | 3.0 | B |
| Ex. 4-6 | 6.0 | C |

A: No damages were confirmed.
B: Damages were slightly confirmed.
C: Damages were confirmed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A recording medium comprising:
   a base material; and
   an ink receiving layer containing inorganic particles and a binder,
   wherein the inorganic particles have an organosilicon structure having silicon;
   a quaternary ammonium group,
   an imino group or a substituted imino group, and
   a hydroxyl group,
   wherein the organosilicon structure has the silicon, the quaternary ammonium group, and the hydroxyl group, from a side close to the inorganic particles, in an order of the silicon, the hydroxyl group, and the quaternary ammonium group.

2. The recording medium according to claim 1, wherein the organosilicon structure has the quaternary ammonium group, the imino group or the substituted imino group, and the hydroxyl group, from a side close to the inorganic particles,
   in an order of the imino group or the substituted imino group, the hydroxyl group, and the quaternary ammonium group or in an order of the hydroxyl group, the imino group or the substituted imino group, and the quaternary ammonium group.

3. The recording medium according to claim 1, wherein the organosilicon structure is a structure represented by General Formula (1),

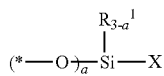

General Formula (1)

wherein a group represented by General Formula (1) is bonded to a surface of the inorganic particles at *, and, in General Formula (1), $R^1$ represents an alkyl group or an aryl group having 1 to 8 carbon atoms, X represents a structure represented by General Formula X, and a is 1, 2, or 3,

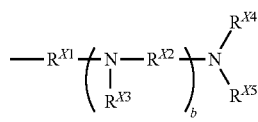

General Formula (X)

wherein, in General Formula X, $R^{x1}$ and $R^{x2}$ each independently represent an alkylene group or an arylene group having 2 to 8 carbon atoms, at least one selected from $R^{x3}$, $R^{x4}$, and $R^{x5}$ represents a structure represented by General Formula Q and other elements represent a hydrogen atom or an alkyl group or an aryl group having 1 to 8 carbon atoms, and b is an integer of 0 to 5,

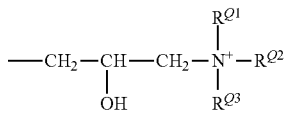

General Formula Q wherein, in General Formula Q, $R^{Q1}$, $R^{Q2}$, and $R^{Q3}$ each independently represent an alkyl group or an aryl group having 1 to 10 carbon atoms.

4. The recording medium according to claim 3, wherein the X in General Formula (1) represents a structure represented by General Formula X-1, a structure represented by General Formula X-2, or a structure represented by General Formula X-3,

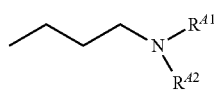

General Formula X-1 wherein, in General Formula X-1, at least one selected from $R^{A1}$ and $R^{A2}$ represents a structure represented by General Formula Q and other elements represent a hydrogen atom or an alkyl group or an aryl group having 1 to 8 carbon atoms,

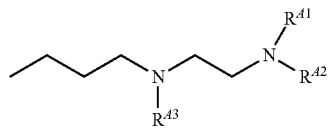

General Formula X-2 wherein, in General Formula X-2, at least one selected from $R^{A1}$, $R^{A2}$, and $R^{A3}$ represents a structure represented by General Formula Q and other elements represent a hydrogen atom or an alkyl group or an aryl group having 1 to 8 carbon atoms,

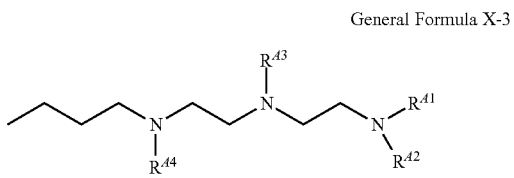

General Formula X-3 wherein, in General Formula X-3, at least one selected from $R^{A1}$, $R^{A2}$, $R^{A3}$, and $R^{A4}$ represents a structure represented by General Formula Q and other elements represent a hydrogen atom or an alkyl group or an aryl group having 1 to 8 carbon atoms.

5. A silane coupling agent, which is used for a recording medium having a base material and an ink receiving layer containing inorganic particles and a binder and which has a structure represented by General Formula (1)',

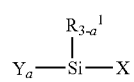

General Formula (1)' wherein, in General Formula (1)', $R^1$ is an alkyl group or an aryl group having 1 to 8 carbon atoms, X represents a structure represented by General Formula X, Y represents a hydrolyzable group, and a is 1, 2, or 3,

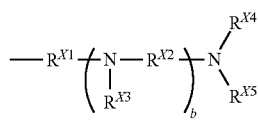

General Formula X wherein, in General Formula X, $R^{x1}$ and $R^{x2}$ each independently represent an alkylene group or an arylene group having 2 to 8 carbon atoms, at least one selected from $R^{x3}$, $R^{x4}$, and $R^{x5}$ represents a structure represented by General Formula Q and other elements represent a hydrogen atom or an alkyl group or an aryl group having 1 to 8 carbon atoms, and b is an integer of 0 to 5,

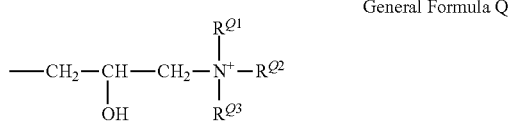

General Formula Q wherein, in General Formula Q, $R^{Q1}$, $R^{Q2}$, and $R^{Q3}$ each independently represent an alkyl group or an aryl group having 1 to 10 carbon atoms.

* * * * *